(12) United States Patent
Sakaguchi et al.

(10) Patent No.: US 9,333,121 B2
(45) Date of Patent: May 10, 2016

(54) DISPOSABLE DIAPER

(71) Applicant: UNICHARM CORPORATION, Shikokuchuo-shi, Ehime (JP)

(72) Inventors: Satoru Sakaguchi, Kanonji (JP); Yasuhiro Yamanaka, Kanonji (JP); Tetsuo Okubo, Kanonji (JP)

(73) Assignee: UNICHARM CORPORATION, Ehime (JP)

( * ) Notice: Subject to any disclaimer, the term of this patent is extended or adjusted under 35 U.S.C. 154(b) by 39 days.

(21) Appl. No.: 14/395,564

(22) PCT Filed: Apr. 25, 2013

(86) PCT No.: PCT/JP2013/062239
§ 371 (c)(1),
(2) Date: Oct. 20, 2014

(87) PCT Pub. No.: WO2013/161951
PCT Pub. Date: Oct. 31, 2013

(65) Prior Publication Data
US 2015/0073374 A1    Mar. 12, 2015

(30) Foreign Application Priority Data

Apr. 27, 2012    (JP) ................. 2012-104151

(51) Int. Cl.
*A61F 13/494*    (2006.01)
*A61F 13/49*     (2006.01)

(52) U.S. Cl.
CPC ......... *A61F 13/494* (2013.01); *A61F 13/49017* (2013.01); *A61F 13/49473* (2013.01);
(Continued)

(58) Field of Classification Search
CPC ................... A61F 13/15203; A61F 13/49007; A61F 13/49009; A61F 13/49017; A61F 2013/15292; A61F 2013/15325; A61F 2013/49022; A61F 2013/49028; A61F 2013/49042; A61F 2013/49046; A61F 2013/49088; A61F 2013/49092; A61F 2013/4948

See application file for complete search history.

(56) References Cited

U.S. PATENT DOCUMENTS 6,482,195 B1    11/2002   Kumasaka
7,972,319 B2     7/2011   Umebayashi et al.
(Continued)

FOREIGN PATENT DOCUMENTS

EP    1723939 A1    11/2006
EP    2438893 A1     4/2012
(Continued)

OTHER PUBLICATIONS

International Search Report mailed Jul. 9, 2013 in International Patent Application No. PCT/JP2013/062239 filed Apr. 25, 2013.
(Continued)

*Primary Examiner* — Lynne Anderson
(74) *Attorney, Agent, or Firm* — Hauptman Ham, LLP (57) ABSTRACT

In a disposable diaper, ends at a front waistline region side of the disposable diaper within a stretchable range in leg stretch units are configured so as to be closer to an end at the front waistline region side as compared to an end at the front waistline region side within a stretchable range in the crotch stretch unit. Ends at a rear waistline region side within the stretchable range in the leg stretch units are configured so as to be closer to an end at the rear waistline region side as compared to an end at the rear waistline region side within the stretchable range in the crotch stretch unit. A tensile modulus of the crotch stretch unit is configured so as to be greater than a tensile modulus of the leg stretch units.

6 Claims, 6 Drawing Sheets

(52) U.S. Cl.
CPC ............... *A61F2013/49028* (2013.01); *A61F 2013/49042* (2013.01); *A61F 2013/4948* (2013.01); *A61F 2013/49088* (2013.01)

(56) References Cited

U.S. PATENT DOCUMENTS

| | | | |
|---|---|---|---|
| 8,361,047 B2 | 1/2013 | Mukai et al. | |
| 2003/0040732 A1* | 2/2003 | Ishikawa | A61F 13/49017 604/385.29 |
| 2009/0312739 A1 | 12/2009 | Umebayahi et al. | |
| 2012/0143162 A1* | 6/2012 | Mukai | A61F 13/15804 604/385.3 |
| 2013/0102982 A1* | 4/2013 | Nakano | A61F 13/49019 604/365 |

FOREIGN PATENT DOCUMENTS

| | | |
|---|---|---|
| JP | 2001-37807 A | 2/2001 |
| JP | 2008-136515 A | 6/2008 |
| JP | 2010-279612 A | 12/2010 |
| TW | 200913970 A | 4/2009 |
| TW | 201108998 A | 3/2011 |
| WO | 2006118214 A1 | 11/2006 |

OTHER PUBLICATIONS

Notification of Reasons for Rejection in corresponding Japanese Application No. 2012-104151 dated Jan. 22, 2013.
Extended European Search Report dated Nov. 11, 2015, corresponding to European Patent Application No. 13782566.7.

* cited by examiner

DISPOSABLE DIAPER

RELATED APPLICATIONS

The present application is a National Phase of International Application Number PCT/JP2013/062239, filed Apr. 25, 2013, which claims priority to Japanese Application Number 2012-104151, filed Apr. 27, 2012.

TECHNICAL FIELD

The present invention relates to a disposable diaper.

BACKGROUND ART

Conventionally, there has been known a disposable diaper having a front waistline region, a rear waistline region, and a crotch region positioned between the front waistline region and the rear waistline region, in which a pair of leg hole openings are formed while an absorber running across the crotch region and extending to the front waistline region and the rear waistline region is provided, and elastic members are arranged along the leg hole openings.

In such a disposable diaper, in order to make it difficult to leave a trace of compression by the elastic members and to prevent leakage of bodily waste, there has been known a technique that tensile stress is changed in accordance with a placement position of each of the elastic members (for example, Patent Literature 1).

CITATION LIST

Patent Literature

[PTL 1] Japanese Unexamined Patent Application Publication No. 2001-37807

SUMMARY OF INVENTION

However, the applicants found out that when movement of a wearer is applied to the disposable diaper in a worn state, it increases the likelihood of the situation where the elastic members arranged along the leg hole openings get entangled between the disposable diaper and the body of the wearer, so that the leakage of bodily waste from the leg hole openings tends to occur.

Therefore, the present invention has been achieved in view of the above-described problem, and an object thereof is to provide a disposable diaper configured to decrease the likelihood of the situation where the elastic members arranged along the leg hole openings get entangled between the disposable diaper and the body of a wearer.

A first aspect of the present invention is a disposable diaper including: a front waistline region; a rear waistline region; a crotch region positioned between the front waistline region and the rear waistline region; a pair of leg hole openings; an absorber running across the crotch region and extending to the front waistline region and the rear waistline region; a product longitudinal direction from the front waistline region towards the rear waistline region; a product widthwise direction perpendicular to the product longitudinal direction; a crotch stretch unit that is formed within an absorber placement region having the absorber placed within the crotch region and is stretchable at least in the product longitudinal direction; and a pair of leg stretch units that are formed along the leg hole openings outside the crotch stretch unit in the product widthwise direction and can expand and contract at least in the product longitudinal direction, wherein: ends at the front waistline region side within a stretchable range in the leg stretch units are configured so as to be closer to an end at the front waistline region side of the disposable diaper as compared to an end at the front waistline region side within a stretchable range in the crotch stretch unit; ends at the rear waistline region side within the stretchable range in the leg stretch units are configured so as to be closer to an end at the rear waistline region side of the disposable diaper as compared to an end at the rear waistline region side within the stretchable range in the crotch stretch unit; and a tensile modulus of the crotch stretch unit is configured so as to be greater than a tensile modulus of the leg stretch units.

DESCRIPTION OF EMBODIMENTS

First Embodiment of Present Invention

With reference to FIGS. 1 to 8, a disposable diaper 10 according to the first embodiment of the present invention is explained.

In the following description of the drawings, the same or similar reference numerals are used to designate the same or similar parts. It will be appreciated that the drawings are schematically shown and the ratio and the like of each dimension are different from the real ones.

Therefore, a specific dimension should be determined in view of the following description. Moreover, among the drawings, the respective dimensional relations or ratios may naturally differ.

Hereinafter, the disposable diaper 10 according to the present embodiment is explained by citing an open-type disposable diaper as an example. However, the disposable diaper 10 according to the present embodiment is not limited to the open-type disposable diaper but is applicable to a pant-type disposable diaper.

Figure 1:
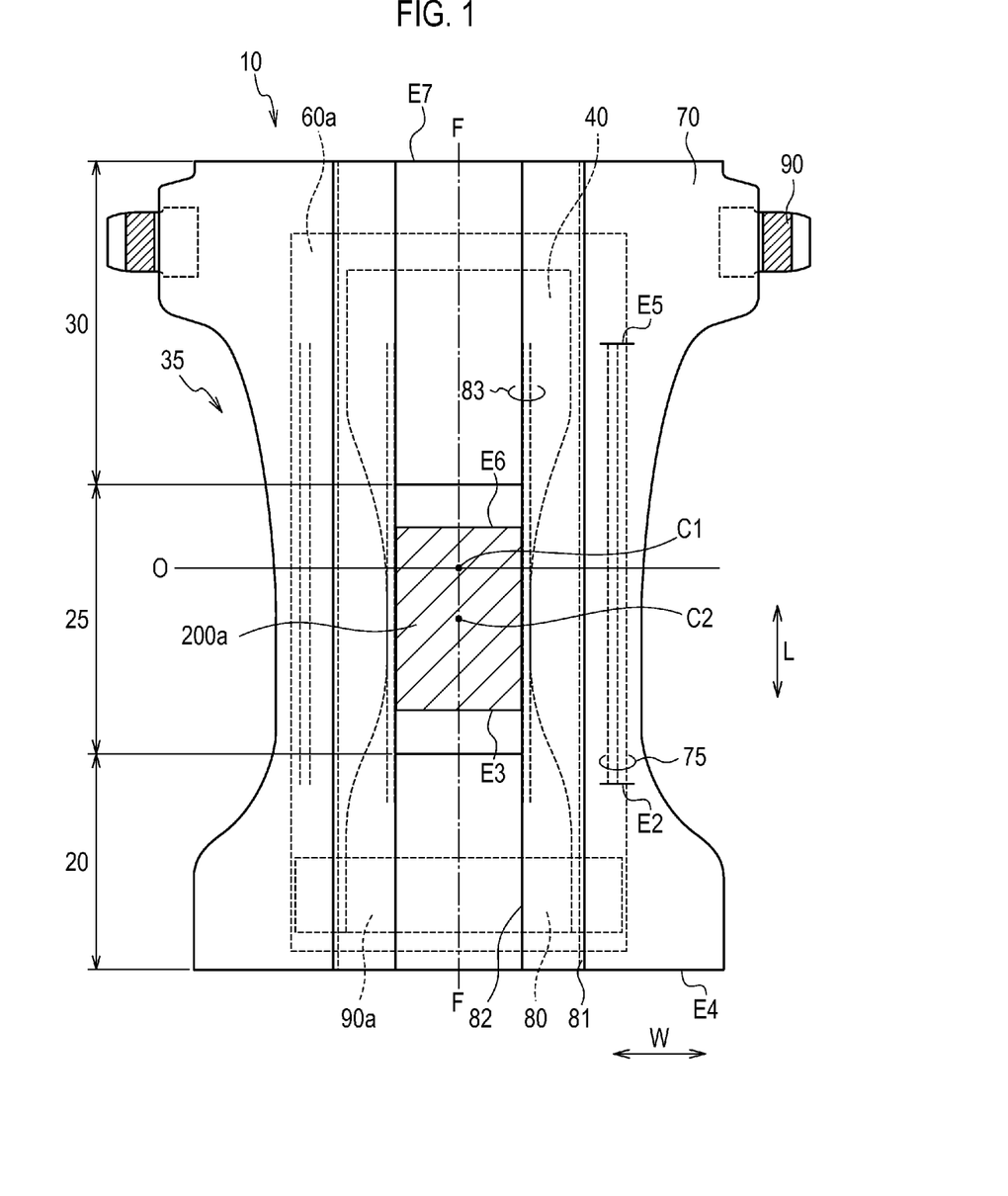
FIG. 1 is an exploded plan view of a disposable diaper according to an embodiment of the present invention.
Figure 2:
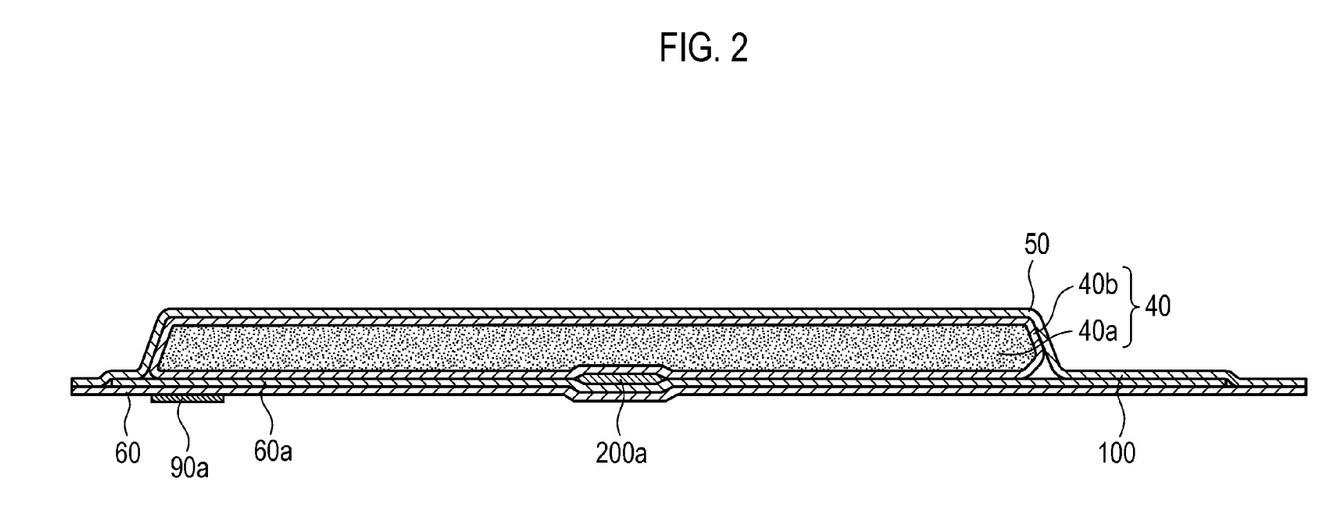
FIG. 2 is an F-F cross-sectional view in an exploded plan view of a disposable diaper according to a first embodiment of the present invention.

FIG. 1 is an exploded plan view of the disposable diaper 10 according to the present embodiment. FIG. 2 is an F-F cross-sectional view of the disposable diaper 10 taken along the line F-F shown in FIG. 1. It should be noted that the exploded plan view of FIG. 1 is a diagram in which leg stretch units 75 and leg side gathers 80 are in an expanded state such that wrinkles are not formed in a topsheet 50 and side flaps 70, for example, that configure the disposable diaper 10.

As shown in FIG. 1, the disposable diaper 10 has a front waistline region 20, a crotch region 25, and a rear waistline region 30. Furthermore, a pair of leg hole openings 35 are formed in the disposable diaper 10.

Herein, the front waistline region 20 is a portion which comes in contact with the front waistline part of a wearer; the rear waistline region 30 is a portion which comes in contact with the rear waistline part of the wearer; and the crotch region 25 is a portion which is positioned between the front waistline region 20 and the rear waistline region 30.

In the present embodiment, the direction from the front waistline region 20 towards the rear waistline region 30 is called the product longitudinal direction L, and the direction perpendicular to the product longitudinal direction L is called the product widthwise direction W.

The disposable diaper 10 is provided with an absorber 40 running across the crotch region 25 and extending to the front waistline region 20 and the rear waistline region 30. As shown in FIG. 2, the absorber 40 is made up of an absorbent core 40a and a core wrap 40b.

The absorbent core 40a is the same as that used in the conventional disposable diaper, and can be configured appropriately by using known components or materials, such as ground pulp and high absorbent polymer. The absorbent core 40a is wrapped in the sheet-shaped core wrap 40b.

The core wrap 40b is a sheet for wrapping the absorbent core 40a. A part of at least the skin contact surface side of the core wrap 40b is made from various fibrous nonwoven fabrics or a tissue sheet having liquid-permeability.

As a member making up the core wrap 40b, for example, an air-through fibrous nonwoven fabric, a spunbond nonwoven fabric, or an SMS (spunbond-meltblown-spunbond) nonwoven fabric having a mass of approximately 10 to 30 g/m$^2$, or a tissue sheet having a mass of approximately 10 to 30 g/m$^2$ can be used.

As shown in FIG. 2, a liquid-permeable topsheet 50 is provided at the top side (skin contact surface side) of the absorber 40, and a liquid-impermeable backsheet 60a is provided at the back side (non-skin contact surface side) of the absorber 40. Furthermore, as shown in FIG. 2, an exterior sheet 60 may be provided at the back side (non-skin contact surface side) of the backsheet 60a.

A side flap 70 is provided at each side edge in the product widthwise direction W of the absorber 40, as shown in FIG. 1. The side flap 70 is made of one or two or more sheets of nonwoven fabric overlapping one another.

As shown in FIG. 1, the disposable diaper 10 is provided with a pair of fastening tapes 90 in the rear waistline region 30 and a target tape 90a in a predetermined region at the non-skin contact surface side of the front waistline region 20.

Herein, by mounting the fastening tapes 90 on the target tape 90a, the disposable diaper 10 can be retained to the body of a wearer.

Furthermore, as shown in FIG. 1, the disposable diaper 10 may be provided with a crotch stretch unit 200a which can expand and contract and formed in an absorber placement region having the absorber 40 placed therein, within the crotch region 25.

Specifically, as shown in FIG. 2, the crotch stretch unit 200a may be provided between the absorber 40 (core wrap 40b) and the backsheet 60a.

Herein, the crotch stretch unit 200a can expand and contract in the product longitudinal direction L but may be stretchable in both the product longitudinal direction L and the product widthwise direction W.

As described above, the crotch stretch unit 200a is placed within the crotch region 25 and is stretchable in the product longitudinal direction L, which decreases the likelihood of the situation where the elastic members making up leg stretch units 75 at the front waistline region 20 side get entangled between the disposable diaper 10 and the body of a wearer at the time of installing the disposable diaper 10.

Furthermore, a center C2 of the crotch stretch unit 200a in the product longitudinal direction L may be deviated from a center C1 of the disposable diaper 10 in the product longitudinal direction L towards the front waistline region 20 side.

At the time of installing the disposable diaper 10, during a stage of placing the disposable diaper 10 under the buttocks of a wearer and pulling it towards the position of the navel of the wearer, the elastic members making up the leg stretch units 75 at the front waistline region 20 side are likely to be entangled between the disposable diaper 10 and the body of the wearer. However, with the structure configured as described above, such entanglement is even less likely to occur.

Furthermore, the crotch stretch unit 200a may be configured so as to extend towards the front waistline region 20 side and the rear waistline region 30 side by running across a center line O of the disposable diaper 10 in the longitudinal direction L.

In the present embodiment, the crotch stretch unit 200a may be made from a stretch sheet member.

Used as such a stretch sheet member are, for example, a stretch film made from thermoplastic elastomer resin such as urethane or styrene melted and shaped in a film form; a stretch nonwoven fabric made from stretch fiber; a composite sheet obtained by binding a non-stretch sheet which is partially cut out or embrittled to a stretch film or a stretch nonwoven fabric; and the like.

Furthermore, instead of using such a stretch sheet member, the crotch stretch unit 200a may be formed by lining up stretchable elastic members shaped in a thread form or a band form, made from polyurethane elastic fiber or natural rubber, in parallel with each other.

The top side (the topsheet 50 side) of the absorber 40 is provided with the pair of leg stretch units (leg gathers) 75 which is formed along the leg hole openings 35 and can expand and contract at least in the product longitudinal direction L.

The leg stretch units 75 are longer than the crotch stretch unit 200a in the product longitudinal direction L while being provided outside the crotch stretch unit 200a in the product widthwise direction W.

For example, as shown in FIG. 1, each of the leg stretch units 75 may be made up of a predetermined number of elastic members (three elastic members in the example shown in FIG. 1).

Furthermore, similarly to the crotch stretch unit 200a, the leg stretch units 75 may be made of a stretch sheet member.

Such a structure allows the leg stretch units 75 to have a wider stretchable range as compared with a case where the leg stretch units 75 are made of elastic members in a thread form. As a result, the disposable diaper 10 can fit in a planar fashion along the leg girth parts of a wearer, which improves close contact between the leg stretch units 75 and the body of the wearer and makes positional shifting less likely to occur with respect to the body of the wearer.

Specifically, a width of the stretch sheet member (a width in the product widthwise direction W of the disposable diaper 10 in a natural state) is preferably 5 mm to 45 mm, more preferably 12.5 mm to 35 mm, at least in the crotch region 25.

Herein, the stretch sheet member having a width smaller than 5 mm does not practically produce an effect of fitting along the leg girth parts of a wearer in a planar fashion, whereas the stretch sheet member having a width greater than 45 mm enlarges a region along the leg girth parts, so that the stretch sheet member is easily entangled with the wearer's body side or rolled up.

Furthermore, the leg stretch units 75 extends up to the ends of the leg hole openings 35, which decreases the likelihood of the situation where the stretch sheet members placed along the leg hole openings 35 get entangled between the disposable diaper 10 and the body of a wearer.

Herein, the structure may be configured so that a frill units made of only a non-stretch member may not be arranged outside the leg stretch units 75 in the product widthwise direction W.

Alternatively, the structure may be configured so that a length in the product widthwise direction of the frill units arranged outside the leg stretch units 75 in the product widthwise direction W in the extended state is smaller than 7 mm. The measurement of the "length" described in the specification will be performed by using a spring measure (tape: covered with glass fiber reinforced vinyl chloride) manufactured by Shinwa Rules Co., Ltd.

Such a structure allows the frill units to be pushed against the body of a wearer up to the edges of the leg hole openings 35 by means of shrinkage force by the leg stretch units 75. However, in a case of a length of the frill units in the product widthwise direction being greater than 7 mm, a degree of freedom of the frill units, at the edge sides of the leg hole openings 35 becomes high enough to cause entanglement to the body of a wearer.

Figure 3:
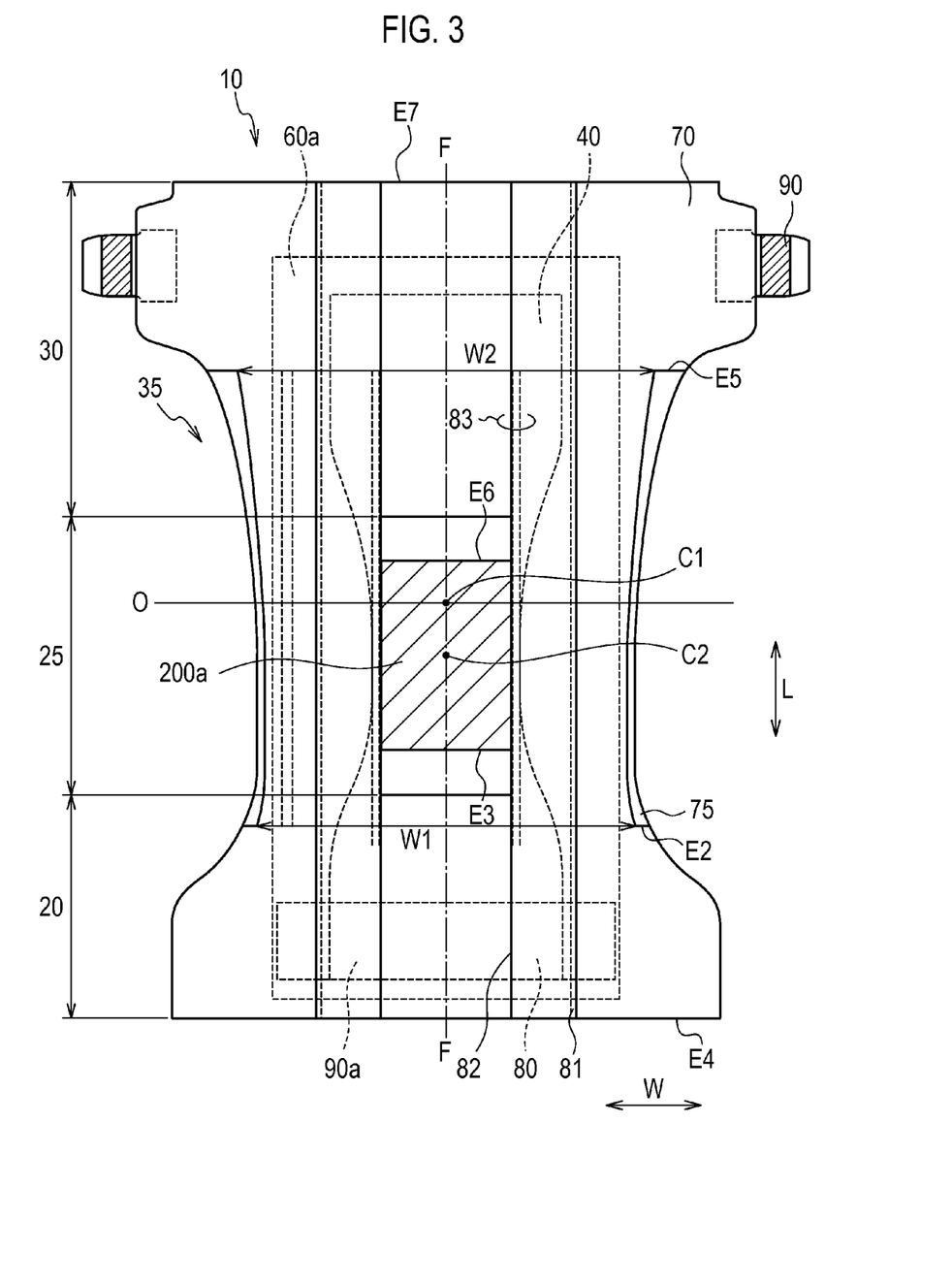
FIG. 3 is an exploded plan view of the disposable diaper according to the embodiment of the present invention.

As shown in FIG. 3, the structure may be configured so that a space between the inner ends in the product widthwise direction W of the pair of left-right leg stretch units 75 becomes larger as extending from the crotch region 25 towards the front waistline region 20 while becoming larger as extending from the crotch region 25 towards the rear waistline region 30.

Such space is obtained by measuring a distance between the inner ends in the product widthwise direction W of the pair of left-right leg stretch units 75 after stretching out and retaining the disposable diaper 10 in the product longitudinal direction L and the product widthwise direction W from the natural state to the state in which wrinkles cannot be visually observed.

In a case of installing the disposable diaper 10 onto the body of a wearer, a shape that an interval between the pair of left-right leg stretch units 75 in the product widthwise direction W is small in the crotch region 25 and becomes larger as extending towards the front waistline region 20 and the rear waistline region 30 allows the leg stretch units 75 to have a better fit along the body line of the wearer, so that the leg stretch units 75 can be placed so as to be stretched out suitably along the leg girth parts of the wearer.

Furthermore, in a case of installing the disposable diaper 10 is onto the body of a wearer, at the time of placing the disposable diaper 10 under the buttocks of the wearer, a length between the pair of left-right leg stretch units 75, that becomes greater as extending towards the rear waistline region 30 side, allows a main body of the disposable diaper 10 to have a wider fit in a planer fashion with respect to the body of the wearer in its widthwise direction as the leg stretch units 75 extend towards the rear waistline region 30 side, thereby making the leg stretch units 75 less likely to be rolled up.

Furthermore, as shown in FIG. 3, the structure may be configured so that an interval W1 between the inner ends in the product widthwise direction W of the pair of leg stretch units 75 in an end E2 at the front waistline region 20 side within a stretchable range in the leg stretch units 75 is smaller than an interval W2 between the inner ends in the product widthwise direction W of the pair of leg stretch units 75 at an end E5 at the rear waistline region 30 side within a stretchable range in the leg stretch units 75.

Furthermore, such an interval is also obtained by measuring a distance between the inner ends in the product widthwise direction W of the pair of left-right leg stretch units 75 after stretching out and retaining the disposable diaper 10 in the product longitudinal direction L and the product widthwise direction W from the natural state to the state in which wrinkles cannot be visually observed.

Herein, a stretch of the skin surface of the wearer's body is large especially in the buttocks and is prominent at the position closer to the outer side in the widthwise direction of the buttocks. Furthermore, the leg stretch units 75 are bought in close contact with the body of a wearer.

Herein, as described above, an trajectory of the leg stretch units 75 at the buttocks side is made longer by setting the length W1 shorter than the length W2, so that even in a case where movement of a wearer is applied to the disposable diaper 10, the disposable diaper 10 can follow movement of the skin of the wearer by stretching the leg stretch units 75 and sagging is less likely to occur in the leg stretch units 75 at the front waistline region 20 side.

Accordingly, with the structure described above, even in a case where movement of a wearer has been applied, the leg stretch unit 75 can keep close contact with the leg girth parts of the wearer more stably, thereby preventing entanglement due to partial sagging of the leg stretch units 75.

Herein, the structure may be configured so that a tensile modulus of the crotch stretch unit 200a is greater than a tensile modulus of the leg stretch units 75.

It is to be noted that a tensile modulus is a modulus for defining how stretchable each area is. For example, such a modulus can be calculated by the following method.

Firstly, an area as a measuring object (the crotch stretch unit 200a or the leg stretch unit 75) is cut out as a sample as it is from a product as a measuring object (the disposable diaper 10).

Specifically, the area is cut out with the non-stretch member joined to the crotch stretch unit 200a or the leg stretch unit 75 being included. Herein, in a region in which the absorber is placed, the absorber itself is cut out.

Secondly, the cut-out sample is kept in ambient atmosphere having a temperature of 20° C. and a relative humidity of 60% in the natural state for 60 minutes, without application of tensile load.

Thirdly, a line L is drawn in the direction of expansion and contraction of the sample, at a center position in the widthwise direction perpendicular to the direction of expansion and contraction and a length of the line L in the natural state is measured. At this time, the line L is drawn on a horizontal board by applying as little load as possible on the sample and a length of the line L is measured. Herein, an initial length of the line L is designated as "A".

Furthermore, in order to minimize a measurement deviation in the sample, it is preferable to draw the line L as long as possible. However, it is necessary to avoid overlapping between an area to be sandwiched in a zipper of a following tensile tester and the line L.

Fourthly, the both end portions in the direction of expansion and contraction of the sample are retained in a tensile tester such as an autograph type tensile tester made by Shimadzu Corporation; the sample is stretched out until application of a load of 0.8 N; and a length of the line L at the time of stretching out is measured to designate a length of the line L in such a state as "A'".

For example, with the tensile tester, the sample is pulled in the direction of expansion and contraction (pulled upward in a vertical direction with respect to the horizontal plane) at tensile speed of 100 mm/min.

Fifthly, a tensile modulus is calculated by the following equation.

$$\text{Tensile Modulus} = (A' - A)/A$$

Herein, the structure may be configured so that the end E2 at the front waistline region 20 side within a stretchable range in the leg stretch units 75 is placed closer to an end E4 at the front waistline region 20 side of the disposable diaper 10, as compared to an end E3 at the front waistline region 20 side within a stretchable range in the crotch stretch unit 200a.

Furthermore, the structure may be configured so that the end E5 at the rear waistline region 30 side within a stretchable range in the leg stretch units 75 is placed closer to an end E7 at the rear waistline region 30 side of the disposable diaper 10, as compared to an end E6 at the rear waistline region 30 side within a stretchable range in the crotch stretch unit 200a.

By defining a relation of a tensile modulus and the ends E2 to E7 as described above, in step S103 to be described later, in a case where the disposable diaper 10 is pulled in the product longitudinal direction L, a state where the leg stretch units 75 are stretched out while the crotch stretch unit 200a is not stretched out cab be maintained.

Furthermore, the structure may be configured so that the amount of shrinkage in the product longitudinal direction L of the crotch stretch unit 200a is set to 2 to 8% of a length in the product longitudinal direction L of the disposable diaper 10.

It is to be noted that the amount of shrinkage represents a difference between a length "b (mm)" of the sample in the stretched-out state where wrinkles are reduced so that the surface of the sample becomes almost smooth and a length "a (mm)" of the sample in the natural state oriented in the stretch direction of the sample, and the amount of shrinkage can be calculated by (b−a).

The inventor of the present invention confirmed that the crotch stretch unit 200a is likely to extend suitably along the body of a wearer during a process of installing the disposable diaper 10 on the wearer, in a case where the amount of shrinkage in the product longitudinal direction L of the crotch stretch unit 200a is set to 2 to 8% of a length in the product longitudinal direction L of the disposable diaper 10.

Herein, in a case of the amount of shrinkage in the product longitudinal direction L of the crotch stretch unit 200a being set greater than 8%, the crotch stretch unit 200a shrinks too much to keep enough length in the product longitudinal direction L of the disposable diaper 10, thereby making it difficult to install the disposable diaper 10 onto the body of a wearer or making it easy to cause shifting due to too close contact between the disposable diaper 10 and the body of the wearer in the crotch region 25.

On the other hand, in a case of the amount of shrinkage in the product longitudinal direction L of the crotch stretch unit 200a being set smaller than 2%, the crotch stretch unit 200a is less likely to produce the effect to bring the disposable diaper 10 close to the body of a wearer.

Furthermore, the inner sides (the sides closer to the center in the product widthwise direction W) of the pair of leg stretch units 75 may be provided with a pair of leg side gathers (solid gathers) 80 extending in the product longitudinal direction L.

Each of the leg side gathers 80 has a joint portion 81 and a free end part 82 which is positioned on the opposite side of the joint portion 81 and has an elastic member 83 placed therein.

Herein, the joint portion 81 may be joined to the topsheet 50, the backsheet 60a, or the exterior sheet 60.

Furthermore, the end in the product longitudinal direction L of the free end part 82 is joined to the topsheet 50. The joint portion 81 is placed between the crotch stretch unit 200a and the leg stretch unit 75 in the product widthwise direction W.

Generally, the crotch region 25 of the disposable diaper 10 sags downward and easily gets away from the body of a wearer at the time of installation.

On the other hand, in the disposable diaper 10 according to the present embodiment, the crotch stretch unit 200a is made of a stretch sheet member to result in a high tensile modulus, thereby allowing the absorber 40 placed in the crotch region 25 to keep extending along the crotch of a wearer longer than the conventional disposable diaper.

On the other hand, the leg stretch units 75 are configured to exist along the leg hole openings 35 and come in close contact with the leg girth parts of a wearer.

Therefore, as described above, placement of the joint portion 81 between the crotch stretch unit 200a and the leg stretch unit 75 allows the leg side gather 80 and the leg stretch unit 75 to rise with the crotch stretch unit 200a extending along the body of a wearer being as a start point, so that the leg side gather 80 and the leg stretch unit 75 can be brought in closer contact with the body of the wearer in turn from the inner side to the outer side in the widthwise direction of the body of the wearer.

When the disposable diaper is worn, each of the leg side gathers 80 rises with the joint portion 81 being as a base end while the free end part 82 comes in contact, as the top portion, with the skin of a wearer.

Hereinafter, with reference to FIGS. 4 to 8, movement at the time of installing the disposable diaper 10 according to the present embodiment on a wearer is explained.

Figure 4:
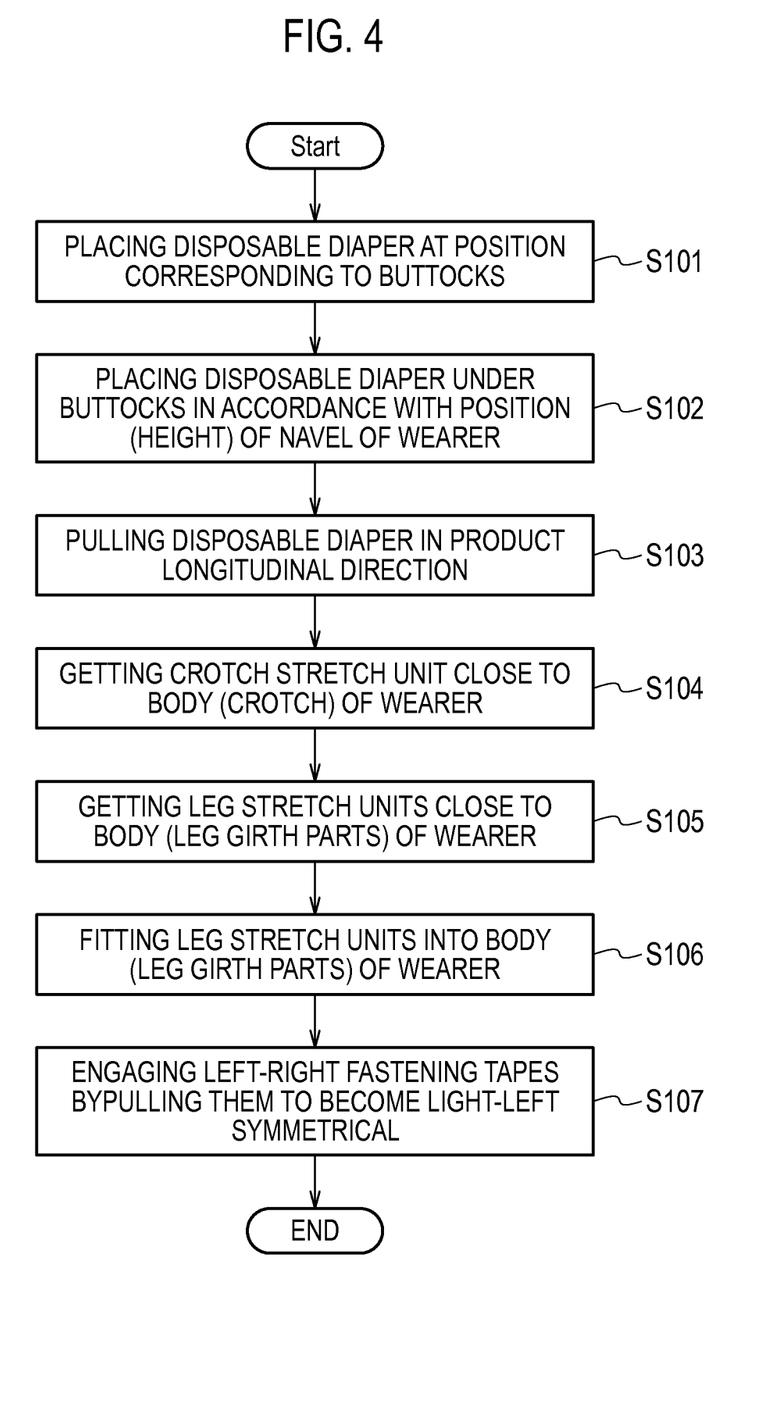
FIG. 4 is a view for illustrating movement at the time of installing the disposable diaper according to the embodiment of the present invention on a wearer.

As shown in FIG. 4, a wearer's helper raises the legs of the wearer to place the disposable diaper at the position corresponding to the buttocks of the wearer in step S101, and places the disposable diaper 10 under the buttocks of the wearer in accordance with the position (height) of the navel of the wearer in step S102.

Herein, in a case where the wearer's helper pulls the disposable diaper 10 in the product longitudinal direction L in step S103, after the crotch stretch unit 200a and the absorber 40 come close to the body (crotch) of a wearer in step S104, the leg stretch units 75 come close to the body (leg girth parts) of the wearer in step S105.

That is, steps S103 to S105 are steps for pulling the disposable diaper 10 towards the position of the navel of the wearer.

Herein, the disposable diaper 10 according to the present embodiment is configured so that a modulus of the crotch stretch unit 200a is larger than that of the leg stretch units 75, so that even in a case where the disposable diaper 10 is pulled in the product longitudinal direction L, the crotch stretch unit 200a is more likely to keep its shrunk state while the leg stretch units 75 are more likely to be stretched out first. Therefore, in the crotch region 25, the crotch stretch unit 200a comes close to the body of a wearer first, and as a result, the leg stretch units 75 come in close contact with the leg girth parts of the wearer after the main body of the disposable diaper 10 including the absorber 40 extends along the body of the wearer.

This results in the increased likelihood of the situation where the leg stretch units 75 extend along the non-skin contact surface side of the disposable diaper 10, thereby decreasing the likelihood of the situation where the leg stretch units 75 get entangled between the disposable diaper and the body of a wearer.

In the existing disposable diaper 10, it is to be noted that the leg stretch units 75 are likely to rise towards the skin contact surface side of the disposable diaper 10, thereby being prone to get entangled in the inner side in the product widthwise direction W of the disposable diaper 10.

Figure 5:
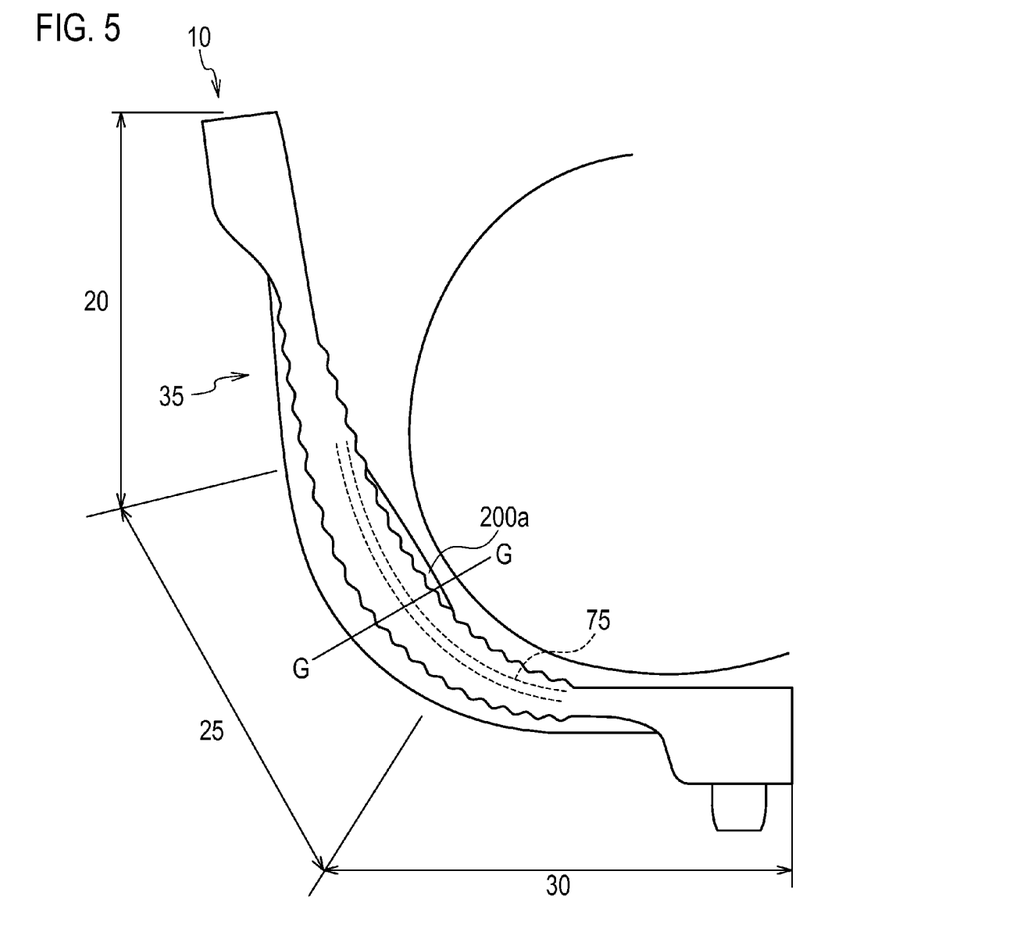
FIG. 5 is a view for illustrating movement at the time of installing the disposable diaper according to the embodiment of the present invention on a wearer.
Figure 6:
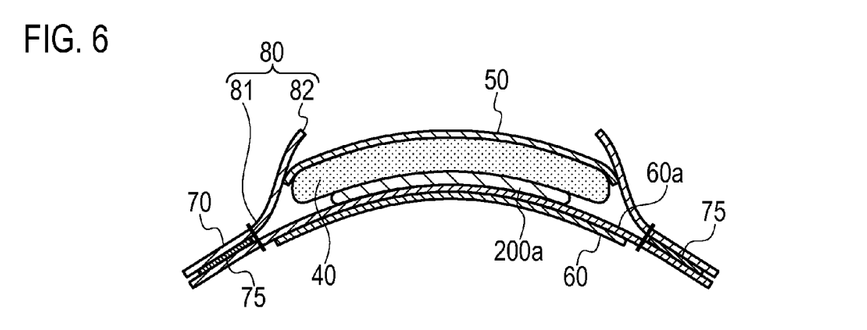
FIG. 6 is a view for illustrating movement at the time of installing the disposable diaper according to the embodiment of the present invention on a wearer.

Therefore, as shown in FIGS. 5 and 6, in step S106, the leg stretch units 75 can fit in an expanded state into the body (leg girth parts) of a wearer without being entangled between the disposable diaper and the body of the wearer. Herein, FIG. 6 is a G-G cross-sectional view of FIG. 5.

Figure 7:
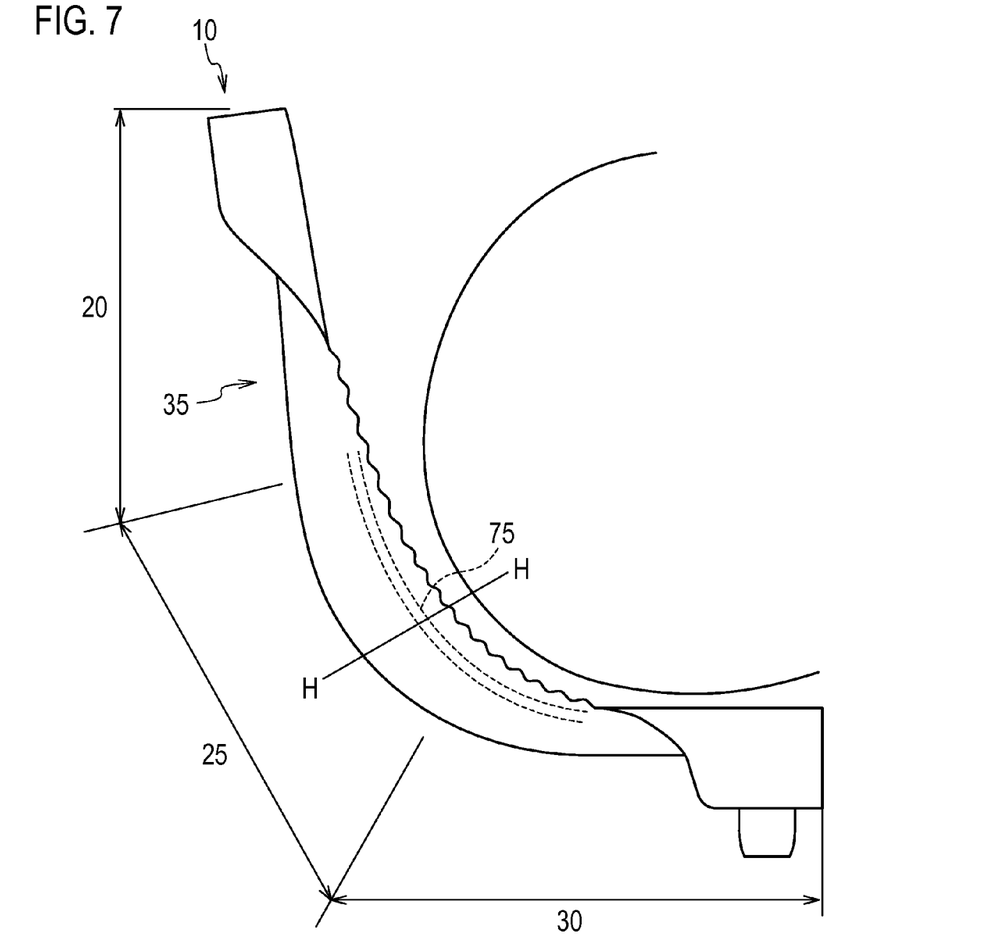
FIG. 7 is a view for illustrating movement at the time of installing an existing disposable diaper on a wearer.
Figure 8:
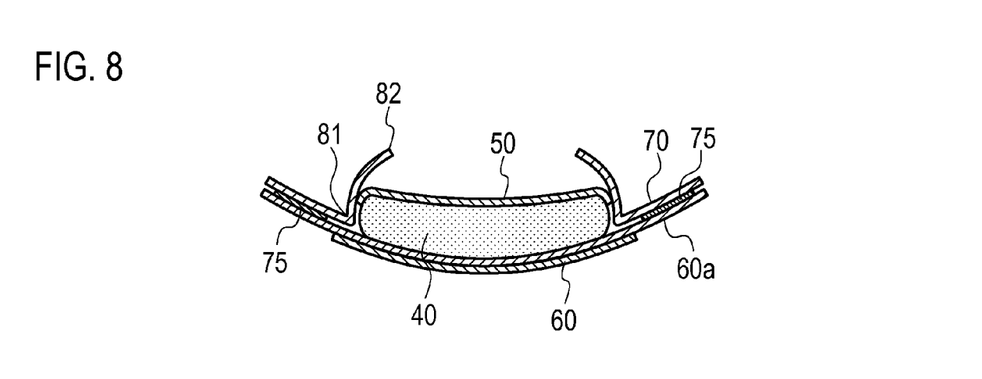
FIG. 8 is a view for illustrating movement at the time of installing the existing disposable diaper on a wearer.

On the other hand, in the existing disposable diaper 10, when a wearer's helper pulls the disposable diaper 10 in the product longitudinal direction L, the leg stretch units 75 come close to the body (leg girth parts) of the wearer first, and then the absorber 40 comes close to the body (crotch) of the wearer. Therefore, as shown in FIGS. 7 and 8, in a case of pulling in the product longitudinal direction L, the likelihood of the situation where the leg stretch units 75 get entangled between the disposable diaper and the body of the wearer is increased. Herein, FIG. 8 is an H-H cross-sectional view of FIG. 7.

It is assumed that this results in increase of cases where the leg stretch units 75 undesirably fit into the body (leg girth parts) of a wearer while being entangled between the disposable diaper and the body of the wearer.

Finally, in step S107, a wearer's helper engages the left-right fastening tapes 90 by pulling them so as to be left-right symmetric.

With the disposable diaper 10 according to the present embodiment, since it is configured so that a tensile modulus of the crotch stretch unit 200a is greater than that of the leg stretch units 75, the crotch stretch units 200a is more likely to keep its shrunk state longer, and even in a case where the disposable diaper 10 is pulled in the product longitudinal direction L, the likelihood of the situation where the leg stretch units 75 get entangled between the disposable diaper and the body of a wearer is small enough to prevent the leakage of bodily waste from the leg hole openings 35 from occurring.

With the disposable diaper 10 according to the present embodiment, even in a case where movement of a wearer is applied to the disposable diaper 10 in a worn state, the likelihood of the situation where the leg stretch units 75 get entangled between the disposable diaper 10 and the body of the wearer is small enough to prevent the leakage of bodily waste from the leg hole openings 35 from occurring.

With the disposable diaper 10 according to the present embodiment, without the need of intricately curving a trajectory of the elastic members making up the leg stretch units 75 along the leg girth parts of a wearer, the leakage of bodily waste from the leg hole openings 35 can be prevented from occurring.

With the disposable diaper 10 according to the present embodiment, the crotch stretch unit 200a forms the bottom in the crotch region 25, that is, the crotch stretch unit 200a is placed closer to the body of a wearer as compared to the leg stretch units 75, so that even if tensile stress of the elastic members making up the leg stretch units 75 is made smaller than that of the conventional disposable diaper, close contact can be improved between the leg stretch units 75 and the leg girth parts of the wearer without leaving a trace of compression by the leg stretch units 75 to the leg girth parts of the wearer.

Thus, the present invention has been explained in detail by using the above-described embodiments; however, it is obvious that for persons skilled in the art, the present invention is not limited to the embodiments explained herein.

Furthermore, in the disposable diaper according to the modification, rather than leg gathers formed from an elastic nonwoven sheet, leg gathers formed from thread-like elastic members may be provided.

The present invention can be implemented as corrected and modified modes without departing from the gist and the scope of the present invention defined by the claims. Therefore, the description of the specification is intended for explaining the example only and does not impose any limited meaning to the present invention.

The entire contents of Japanese Patent Application No. 2012-104151 (filed on Apr. 27, 2012) are incorporated in the present specification by reference.

INDUSTRIAL APPLICABILITY

It is possible to provide a disposable diaper configured to decrease the likelihood of the situation where the elastic members arranged along the leg hole openings get entangled between the disposable diaper and the body of a wearer.

REFERENCE SIGNS LIST

10 . . . disposable diaper
20 . . . front waistline region
25 . . . crotch region
30 . . . rear waistline region
35 . . . leg hole opening
40 . . . absorber
40a . . . absorber core
40b . . . core wrap
50 . . . topsheet
60a . . . backsheet
60 . . . exterior sheet
70 . . . side flap
75 . . . leg stretch unit
80 . . . leg side gather
81 . . . joint portion
82 . . . free end part
90 . . . fastening tape
90a . . . target tape
200a . . . crotch stretch unit

The invention claimed is:

1. A disposable diaper comprising:
a front waistline region;
a rear waistline region;
a crotch region positioned between the front waistline region and the rear waistline region;
a pair of leg hole openings;
an absorber running across the crotch region and extending to the front waistline region and the rear waistline region;
a product longitudinal direction from the front waistline region towards the rear waistline region;
a product widthwise direction perpendicular to the product longitudinal direction;
a crotch stretch unit that is formed within an absorber placement region having the absorber placed within the crotch region and is stretchable at least in the product longitudinal direction; and
a pair of leg stretch units that are formed along the leg hole openings outside the crotch stretch unit in the product widthwise direction and can expand and contract at least in the product longitudinal direction, wherein:
ends at the front waistline region side within a stretchable range in the leg stretch units are configured so as to be closer to an end at the front waistline region side of the disposable diaper as compared to an end at the front waistline region side within a stretchable range in the crotch stretch unit;

ends at the rear waistline region side within the stretchable range in the leg stretch units are configured so as to be closer to an end at the rear waistline region side of the disposable diaper as compared to an end at the rear waistline region side within the stretchable range in the crotch stretch unit; and a tensile modulus of the crotch stretch unit is configured so as to be greater than a tensile modulus of the leg stretch units.

2. The disposable diaper according to claim 1, wherein the crotch stretch unit is configured so as to span a center line in the product longitudinal direction of the disposable diaper and extend towards the front waistline region side and the rear waistline region side.

3. The disposable diaper according to claim 1, wherein an interval between inner ends in the product widthwise direction of the pair of leg stretch units is configured so as to become larger as extending from the crotch region towards the front waistline region or the rear waistline region.

4. The disposable diaper according to claim 1, wherein:

the leg stretch units are made of stretch sheet members; and no frill unit made of only non-stretch member is arranged outside the leg stretch units in the product widthwise direction.

5. The disposable diaper according to claim 3, wherein an interval between inner ends in the product widthwise direction of the pair of leg stretch units, in ends at the front waistline region side within a stretchable range in the leg stretch units is configured so as to be smaller than an interval between inner ends of the pair of leg stretch units in the product widthwise direction in ends at the rear waistline region side within a stretchable range in the leg stretch units.

6. The disposable diaper according to claim 1, wherein a length in the product widthwise direction of a frill unit arranged outside the leg stretch units in the product widthwise direction is configured to be smaller than 7 mm.

* * * * *